United States Patent [19]
Martin et al.

[11] Patent Number: 5,804,400
[45] Date of Patent: Sep. 8, 1998

[54] ELECTROCHEMILUMINESCENT ASSAY

[75] Inventors: Mark Martin, North Bethesda; Liwen Dong, Rockville, both of Md.

[73] Assignee: Igen International, Inc., Gaithersburg, Md.

[21] Appl. No.: 596,830

[22] Filed: Feb. 5, 1996

[51] Int. Cl.$^6$ .............................. C12Q 1/34; C12Q 1/37; G01N 33/53; C12N 1/44

[52] U.S. Cl. .............................. 435/18; 435/975; 435/23; 435/19; 435/817; 435/968; 205/255; 205/257; 205/264; 420/461; 420/462

[58] Field of Search ................................ 435/18, 975, 23, 435/19, 817, 968; 205/255, 257, 264; 420/461, 462

[56] References Cited

U.S. PATENT DOCUMENTS

| | | | |
|---|---|---|---|
| 5,061,455 | 10/1991 | Brose et al. | 435/18 |
| 5,068,088 | 11/1991 | Hall et al. | 435/18 |
| 5,093,268 | 3/1992 | Leventis et al. | 435/18 |
| 5,147,806 | 9/1992 | Kamin et al. | 435/18 |
| 5,221,605 | 6/1993 | Bard et al. | 435/18 |
| 5,235,808 | 8/1993 | Taylor | 435/18 |
| 5,310,687 | 5/1994 | Bard et al. | 435/18 |

OTHER PUBLICATIONS

Yang et al., Bio/Technology, 12, pp. 193–194 (Feb. 1994).
Massey, Biomedical Products, Oct., 1992.
Blackburn et al. (1991) Clin. Chem. 37/9, pp. 1534–1539.
Leland et al. (1990) J. Electrochem. Soc. 137:3127–31.
R. A. Krause, Structure & Bonding, vol. 67, pp. 1–52.
Juris, A. et al, Coord. Chem. Rev, 1988, 3084, 85–277.
Barker, D. L., Jencks, W. P. Biochemistry, 1969, 8, 40; pp. 3879–3889.
Binkley, F; Tortesic; Arch. Biochem. Biophys., 1960, 86, 201.
Enzymes, M. Dixon & E.C. Webb, 3rd ed. 1979, Academic Press, New York.
Latt et al, Biochem (1971), 10, pp. 4263–4270.
B. Holmquist et al, Biochem (1975), 14, pp. 1454–1461.

*Primary Examiner*—Louise N. Leary
*Attorney, Agent, or Firm*—Whitman Breed Abbott & Morgan LLP

[57] ABSTRACT

A rapid single step assay suitable for the detection or quantification of enzymes, in particular, hydrolases, especially, aminopeptidases and esterases. The enzymatic reaction causes the cleavage of a metal ligand labelled hydrolase substrate. The cleaved ligand alters the electrochemiluminescence of bidentate aromatic heterocyclic nitrogen-containing ligand reagent. The change in electrochemiluminescence correlates to the presence of hydrolase activity present in the sample. The assay can be performed on an IGEN Origen® Analyzer.

48 Claims, 7 Drawing Sheets

| COMPOUND | STRUCTURE | RELATIVE ECL |
|---|---|---|
| 1 | pyridine-2-carboxylate (COO⁻) | 59.8 |
| 2 | pyridine-2-carbaldehyde | 37.6 |
| 3 | 2-mercaptopyridine (SH) | 12.3 |
| 4 | ethyl pyridine-2-carboxylate | 11.5 |
| 5 | 2-(hydroxymethyl)pyridine | 8.0 |
| 6 | pyridine-2-carboxamide | 7.3 |
| 7 | 3-(hydroxymethyl)pyridine | 2.4 |
| 8 | 4-(hydroxymethyl)pyridine | 2.2 |
| BACKGROUND ECL | | 1.0 |

| COMPOUND | STRUCTURE | RELATIVE ECL |
|---|---|---|
| 9 | quinoline-8-yl-NH-C(=O)-CH(NH₂)-CH₂-CH(CH₃)₂ | 48.1 |
| 10 | 8-aminoquinoline | 4.6 |
| 11 | quinoline-8-yl-NH-C(=O)-CH(NH-CBZ)-CH₂-CH(CH₃)₂ | 3.3 |
| BACKGROUND ECL | | 1.0 |

ELECTROCHEMILUMINESCENT ASSAY

BACKGROUND OF THE INVENTION

1. Field of the Invention

The present invention relates generally to the development of an electrochemiluminescence (ECL) based assays and reagent test kits for the detection and the quantitative measurement of enzymes, in particular, hydrolases, e.g. esterase and aminopeptidases.

2. Background of the Invention

Assays based on ECL are well known in the art and are finding expanding applications because of their accuracy, ease of use and freedom from radioactive materials.

A particularly useful ECL system is described in a paper by Yang et al, *Bio/Technology*, 12, pp. 193–194 (February 1994). See also a paper by Massey, *Biomedical Products*, October 1992 as well as U.S. Pat. Nos. 5,235,808 and 5,310,687, the contents of these papers and patents being incorporated herein by reference.

ECL processes have been demonstrated for many different molecules by several different mechanisms. In Blackburn et al (1991) *Clin.Chem.* 37/9, pp. 1534–1539, the authors used the ECL reaction of ruthenium (II) tris (bipyridyl), $Ru(bpy)_3^{2+}$, with tripropylamine (TPA) (Leland et al (1990) *J. Electrochem. Soc.* 137:3127–31) to demonstrate the technique. Salts of $Ru(bpy)_3^{2+}$ are very stable, water-soluble compounds that can be chemically modified with reactive groups on one of the bipyridyl ligands to form activated species with which proteins, haptens, and nucleic acids are readily labeled. The activated form of the $Ru(bpy)_3^{2+}$ used by Blackburn et al was $Ru(bpy)_3^{2+}$-NHS ester:

Enzyme assays for hydrolases are well known in the art. See, for example, U.S. Pat. Nos. 5,362,627, 5,221,606, 4,963,815, 4,952,495, 4,931,223, 4,748,116 and 4,657,855. However, none of these employ a electrochemiluminescent signal in the measuring process. Rather, these systems are chemiluminescent, chromophoric or fluorescent based. There remains a need for an relatively simple and accurate hydrolase assay having sensitivity in the picomolar range.

SUMMARY OF THE INVENTION

The invention disclosed within this application achieves sensitivity in the picomolar range for the measurement of enzyme analytes, e.g. hydrolases such as aminopeptidases and esterases. It utilizes electrochemiluminescence and other methodologies, e.g. circular dichroism (CD), magnetic circular dichroism (MCD), electron paramagnetic resonance (EPR), and nuclear magnetic resonance (NMR) spectroscopy to detect a mixed ligand metal containing complex. The detected mixed ligand complex is formed by the interaction of a released or generated ligand with the detectant ligand complex (reagent), e.g. a Ru-containing compounds. The released or generated ligand is formed by the action of the enzyme analyte on the metal binding ligand detectant derivative, e.g. ligand labelled substrate. The interaction of the released or generated ligand includes displacement of an existing ligand from the ligand detectant complex (reagent) which causes a measurable change, e.g. spectral property, molecular weight. Any property which changes in the detectant reagent or is unique to the detected mixed ligand complex formed by the presence of the enzyme analyte is a suitable parameter for measurement.

The invention more specifically contemplates an electrochemiluminesence based assay for the detection of enzymes based on the enzymatic generation of a mixed ligand complex which has a changed electrochemiluminescence signal relative to the original ruthenium or osmium containing ligand detectant complex.

The change in electrochemiluminescent signal can vary from enhancement of the signal to its loss relative to the added detectant ligand complex. It is also contemplated that a signal unique to the formed mixed ligand complex could also be monitored. The presence and amount of the enzyme, e.g. hydrolase, correlates with the electrochemiluminescent signal.

The enzyme analyte releases a ligand label connected to the substrate or acts directly on a ligand substrate to effect its ability to complex with metals such as ruthenium or osmium. (For a review of ruthenium ligand complexes, see R. A. Krause, Structure & Bonding, Vol. 67, pp. 1–52.) The contents of this reference and those appearing hereinafter are expressly incorporated by reference.

In particular, sensitive enzyme assays are described which utilizes enzymatic substrates derivatized with metal-binding ligands. The analyte enzyme catalyzes changes in the abilities of substrates to bind to the non-electrochemiluminescent complex ruthenium (II) bis(bipyridyl), $Ru(bpy)_2^{2+}$, to form electrochemiluminescent mixed ligand complexes. A highly electrochemiluminescent mixed ligand complex was formed between $Ru(bpy)_2^{2+}$ and picolinic acid (1) but not picolinic acid ethyl ester 2-pyridinecarboxylic acid ethyl ester (4), permitting the detection of 2-pyridinecarboxylic acid ethyl ester (4) hydrolysis by pig liver esterase. Other metal ligands and enzymes are envisioned. Electrochemiluminescence (ECL) differences between $Ru(bpy)_2^{2+}$ mixtures of picolinic acid (1) and 2-pyridinecarboxylic acid ethyl ester (4) were detected to a lower concentration limit of 65 pM. Under the conditions used in actual enzyme assays, it was possible to detect 4.4 pM PLE and the hydrolysis of 1.3 $\mu$M 2-pyridinecarboxylic acid ethyl ester (4). In a second assay, leucine aminopeptidase (LAP) hydrolyzed 8-(L)-leucylaminoquinoline (9) to leucine and 8-aminoquinoline (10). A mixed-ligand complex formed between 8-(L)-leucylaminoquinoline (9) and $Ru(bpy)_2^{2+}$ was substantially more electrochemiluminescent than a complex of $Ru(bpy)_2^{2+}$ and 8-aminoquinoline (10). ECL differences between $Ru(bpy)_2^{2+}$ mixtures of 8-(L)-leucylaminoquinoline (9) and 8-aminoquinoline (10) were detectable to 65 nM. Under actual enzyme assay conditions, 375 pM LAP could be detected and hydrolysis of 1.3 $\mu$M 8-(L)-leucylaminoquinoline (9).

Other sensitive detection methods could be used in leu of ECL to measure a property which changes in the detectant reagent or is unique to the mixed ligand complex formed by the presence of the enzyme analyte. These include circular dichroism (CD), magnetic circular dichroism (MCD), electron paramagnetic resonance (EPR), and nuclear magnetic resonance (NMR) spectroscopy. In using these methods, the enzyme reaction and the complex formation steps would be followed by appropriate detection protocols. However, different metals such as cobalt or iron could be used (instead of ruthenium) as well as different ligands (instead of bipyridine). Because ECL would not be used, the final (enzyme-triggered) mixed-ligand complexes would not have to be electrochemiluminescent. However, the initial ligand complex have the requirement of binding an enzyme-triggered ligand to form a complex that differs substantially in the detected spectroscopic result. The essential criteria would be the same as in the ECL method; an enzyme would recognize and catalyze a ligand-labeled substrate or product would then bind to some metal complex, and the binding would be sensitively detectable by some method that detects changes in the environment of the metal. Other objects of the invention will also be apparent from the description of the invention which follows.

DETAILED DESCRIPTION OF THE PREFERRED EMBODIMENTS

Some ruthenium complexes are electrochemiluminescent, a property that permits their detection in sub-picomolar concentrations.[1] Here a new type of enzyme assay using substrates labelled with metal-binding ligands are described.

Enzyme catalysis substantially change the ability of the tested substrates to bind to the non-electrochemiluminescent compound ruthenium(II) bis(bipyridyl) Ru(bpy)$_2$$^{2+}$ to form electrochemiluminescent mixed ligand complexes. In assays involving hydrolytic enzymes, pig liver esterase (PLE; EC 3.1.1.1)[2] and porcine kidney leucine aminopeptidase (LAP; Type IV-S; EC 3.411.2)[3] substantially affected the abilities of their cognate ligand labelled substrates to form electrochemiluminescent ruthenium complexes. This work demonstrates that, when coupled to an appropriate detection system, enzyme-catalyzed ligand alteration can be a highly sensitive means of detecting low levels of substrate turnover.

[1] (1) Juris, A.; Barigelletti, F.; Camagna, S.; Blzani, V.; Elser, P.; VoZelewsky, A. Coord. Chem. Rev., 1988, 3084, 85-277.
(2) Blackburn, G. F.; Shah, H.P.; Kenten, J. H.; Leland, J.; Kamin, R.A.; Link, J.; Peterman, J.; Powell, M. J., Shah, A.; Talley, D. B.; Tyagi, S. K.; Wilkins, E.; Wu, T. G.; Massey R. J. Clin Chem, 1991, 37, 1534–1539.
(3) Yang, H.; Leland, J. K.; Yost, D.; Massey, R. J. Bio/Technology 1994, 12, 193–194.
[2] Barker, D. L.; Jencks, W. P. Biochemistry, 1969, 8, 403879–3889.
[3] Binkley, F.; Tortes, C. Arch. Biochem. Biophys., 60, 86, 201.

Figure 3:
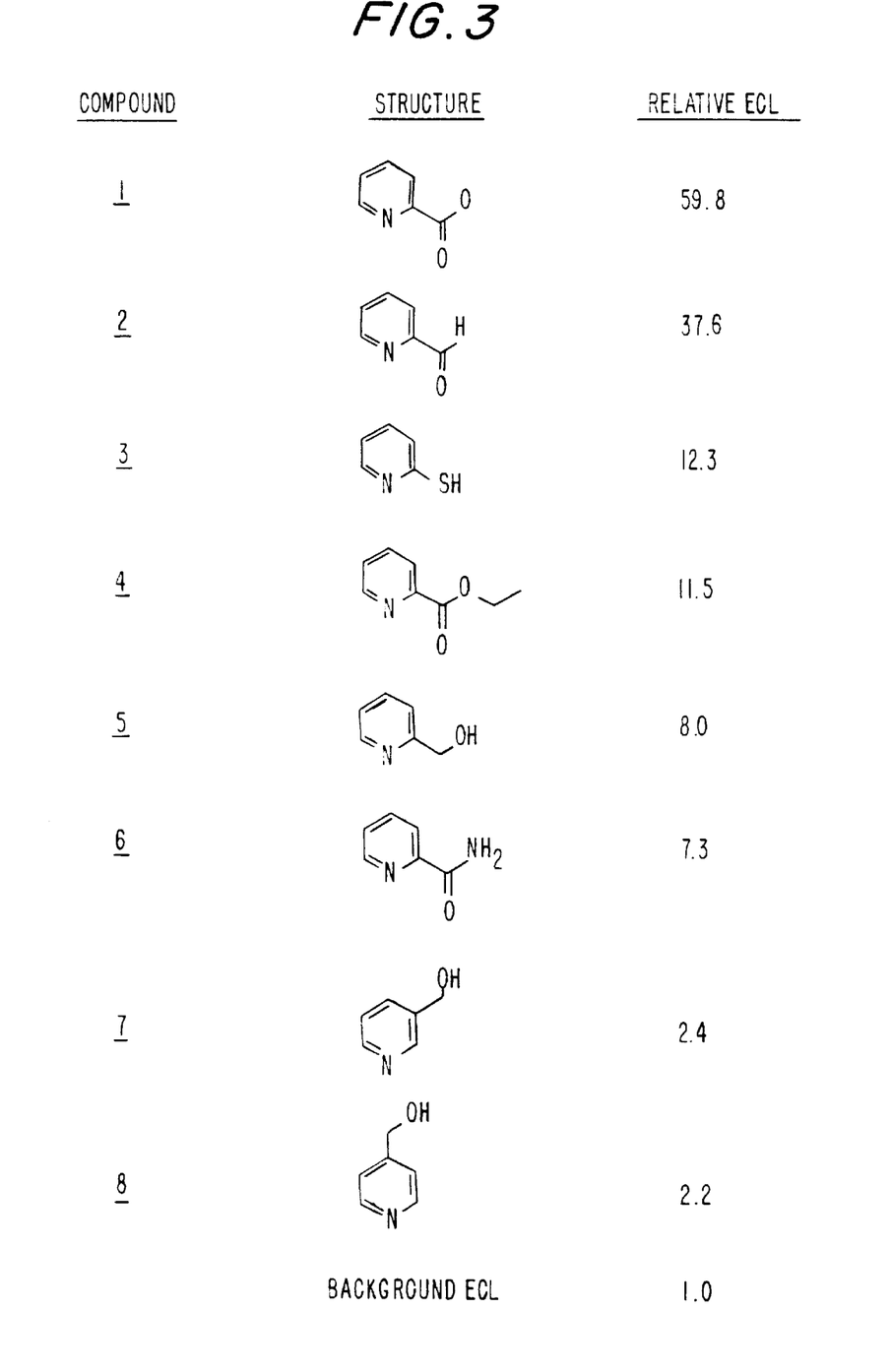
FIG. 3 shows the effect of substituted pyridines on the ECL of Ru(bpy)$_2$$^{2+}$. Compounds (130 μM) were incubated with Ru(bpy)$_2$Cl$_2$ (400 μM) in 80 mM sodium phosphate, pH 8.0, for 60 minutes at 65° C., then diluted into instrument buffer and ECL was measured (as described in Example "0.5"). The substituted pyridines shown are 2-pyridinecarboxylic acid (picolinic acid) (1), 2-pyridinecarboxalehyde (2), 2-mercaptopyridine (3), 2-pyridinecarboxylic acid ethyl ester (4), 2-pyridylcarbinol (5), 2-pyridinecarboxamide (picolinamide) (6), 3-pyridylcarbinol (7) and 4-pyridylcarbinol (8).
Figure 4:
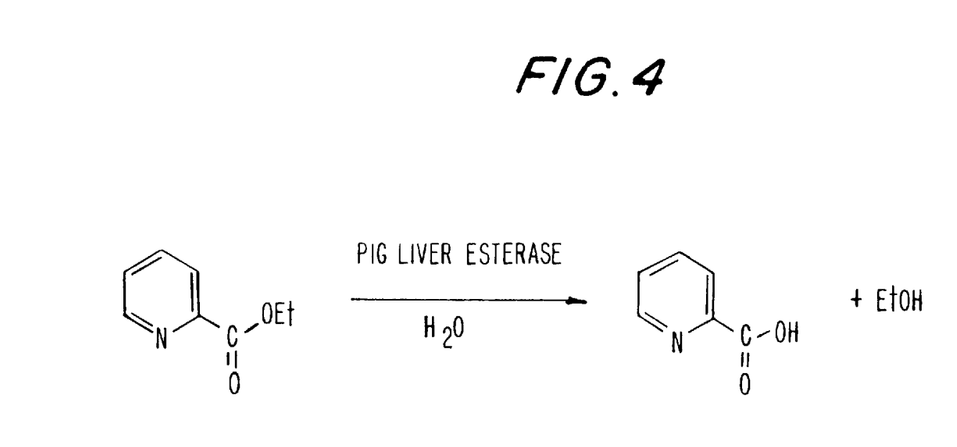
FIG. 4 illustrates the conversion of a picolinic acid ester to the corresponding free acid and alcohol using pig liver esterase.

The abilities of a number of compounds to form electrochemiluminescent mixed-ligand with Ru(bpy)$_2$$^{2+}$ were tested. Substantial differences in electrochemiluminescence (ECL) were found between mixtures of various substituted pyridines and Ru(bpy)$_2$Cl$_2$ (FIG. 3, see also Example "0.5"). Because not all ruthenium complexes are electrochemiluminescent, for a compound in FIG. 3 to be detectable it must fulfill two necessary criteria; it must bind to Ru(bpy)$_2$$^{2+}$ and the resulting complex must be electrochemiluminescent. Generally, the data demonstrate the importance of a good metal-binding substituent in the 2-position for formation of electrochemiluminescent complexes with Ru(bpy)$_2$$^{2+}$ (see, for example, picolinic acid (1) vs. 4-pyridylcarbinol (8)). Some of the observed ECL variations may result from differences in binding rates between certain ligands. However, these data suggest that an enzyme could be sensitively detected if it could catalytically alter the ability of a ligand labelled substrate to form an electrochemiluminescent mixed ligand complex with Ru(bpy)$_2$$^{2+}$. Although the differences in ECL among the compounds shown in FIG. 3 are not spectacular, the inherent sensitivity of the method permits their differentiation to extremely low concentrations. For example, ECL differences between Ru(bpy)$_2$$^{2+}$ complexes of 2-pyridinecarboxylic acid ethyl ester (4) and its hydrolysis product picolinic acid (1) could be differentiated to a detection limit of 65 pM (see Example "1.5"). Reversed-phase HPLC analysis showed that insignificant hydrolysis of 2-pyridinecarboxylic acid ethyl ester 2-pyridinecarboxylic acid ethyl ester (4) occurred during the complex-forming incubations.

Type I Assay

Figure 1:
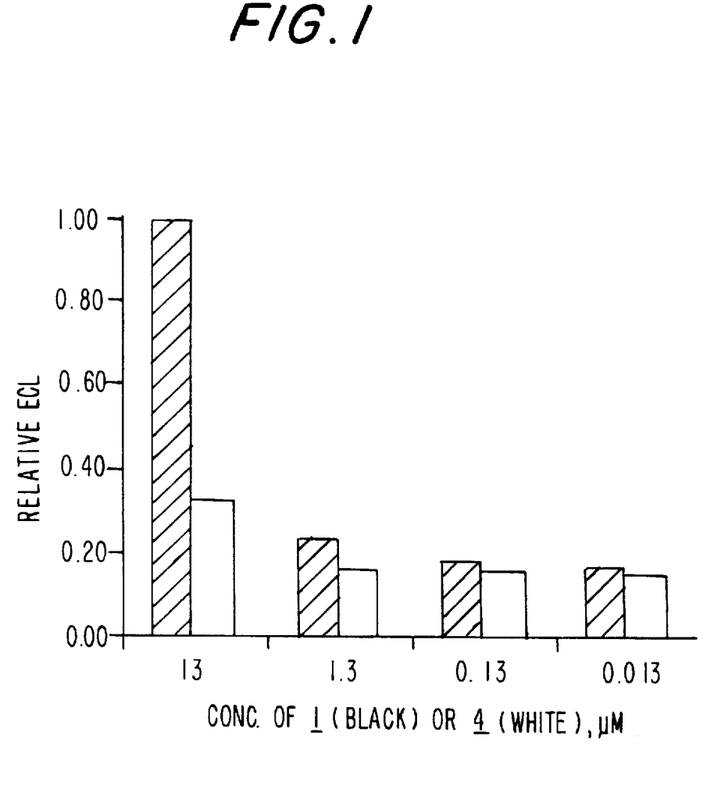
FIG. 1 illustrates ECL detection of mixtures of Ru(bpy)$_2$Cl$_2$ and various concentrations of either picolinic acid (1) (black bars) or 2-pyridinecarboxylic acid ethyl ester (4) (white bars). Mixtures of the designated concentrations of picolinic acid (1) or 2-pyridinecarboxylic acid ethyl ester (4) and 80 μM Ru(bpy)$_2$Cl$_2$ in ECL instrument buffer were heated for 3 hours at 65° C., then diluted into instrument buffer, and ECL was measured.

The difference in ECL properties between Ru(bpy)$_2$$^{2+}$ mixtures of picolinic acid (1) and 2-pyridinecarboxylic acid ethyl ester 2-pyridinecarboxylic acid ethyl ester (4) were exploited in an assay of pig liver esterase activity. PLE was found to efficiently hydrolyze 2-pyridinecarboxylic acid ethyl ester (4) to form the products picolinic acid (1) and ethanol ($K_{cat}$=193 min$^{-1}$ and $K_m$=286 μM) (Scheme I) (see Example 5). Using a protocol compatible with sensitive detection of enzyme activity, ECL differences between mixtures of Ru(bpy)$_2$$^{2+}$ and picolinic acid (1) and 2-pyridinecarboxylic acid ethyl ester (4) could be detected to a lower limit of 1.3 μM (FIG. 1). Under these conditions (see Example 2), the lowest PLE concentration tested, 4.4 pM, was clearly detectable using 13 μM as an initial substrate concentration. This concentration of enzyme completely hydrolyzed 13 μM 2-pyridinecarboxylic acid ethyl ester (4) indicating that even lower enzyme concentrations could be detected (data not shown).

Type II Assay

Figure 5:
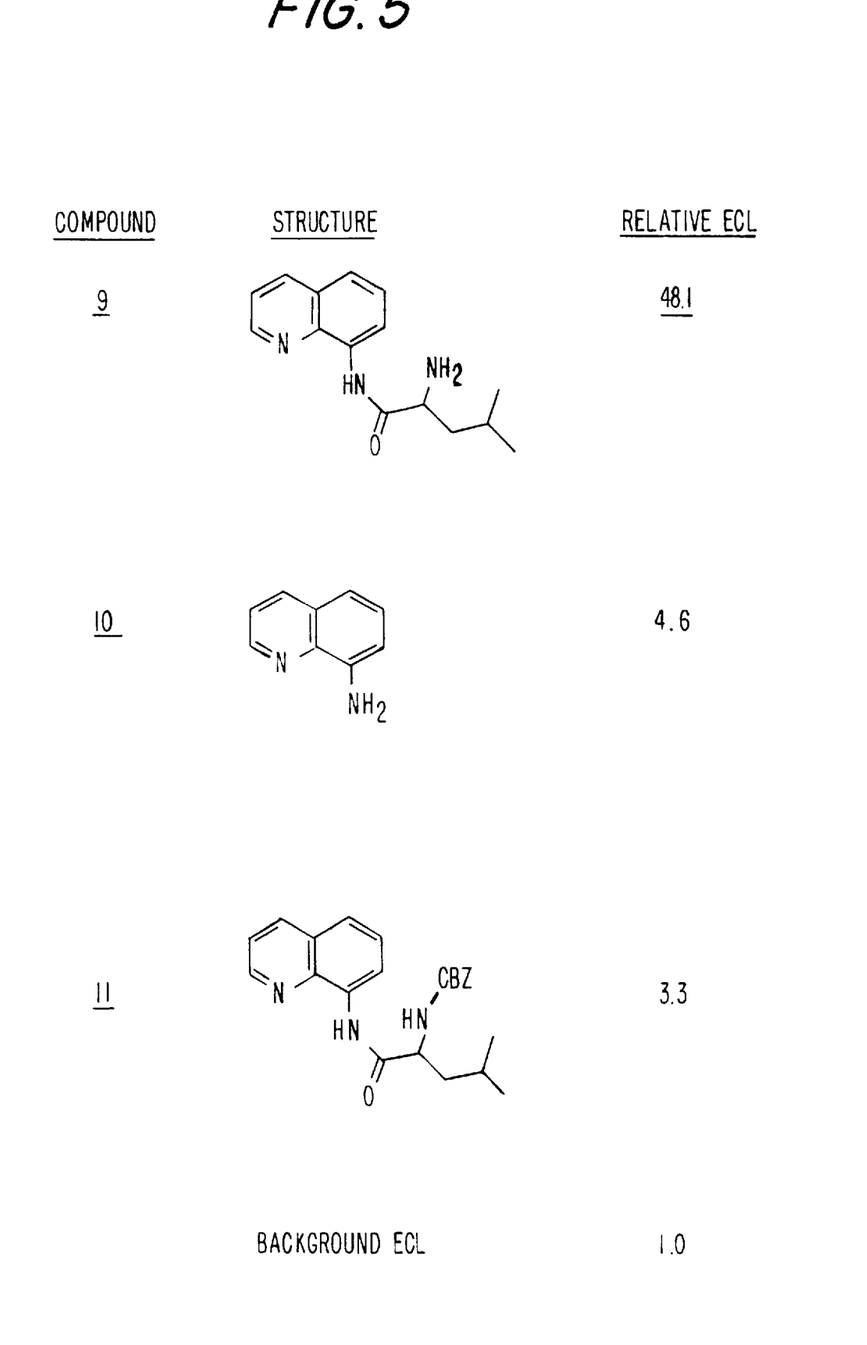
FIG. 5 shows the effect of aminoquinolines on the ECL of Ru(bpy)$_2$$^{2+}$. The experiment was carried out as described in Example 4. The aminoquinolines shown are 8-(L)-leucylaminoquinoline (9), 8-aminoquinoline (10) and CB2-8-(L)-leucylaminoquinoline (11). Values of relative ECL can be validly compared between FIGS. 3 and 5.
Figure 6:
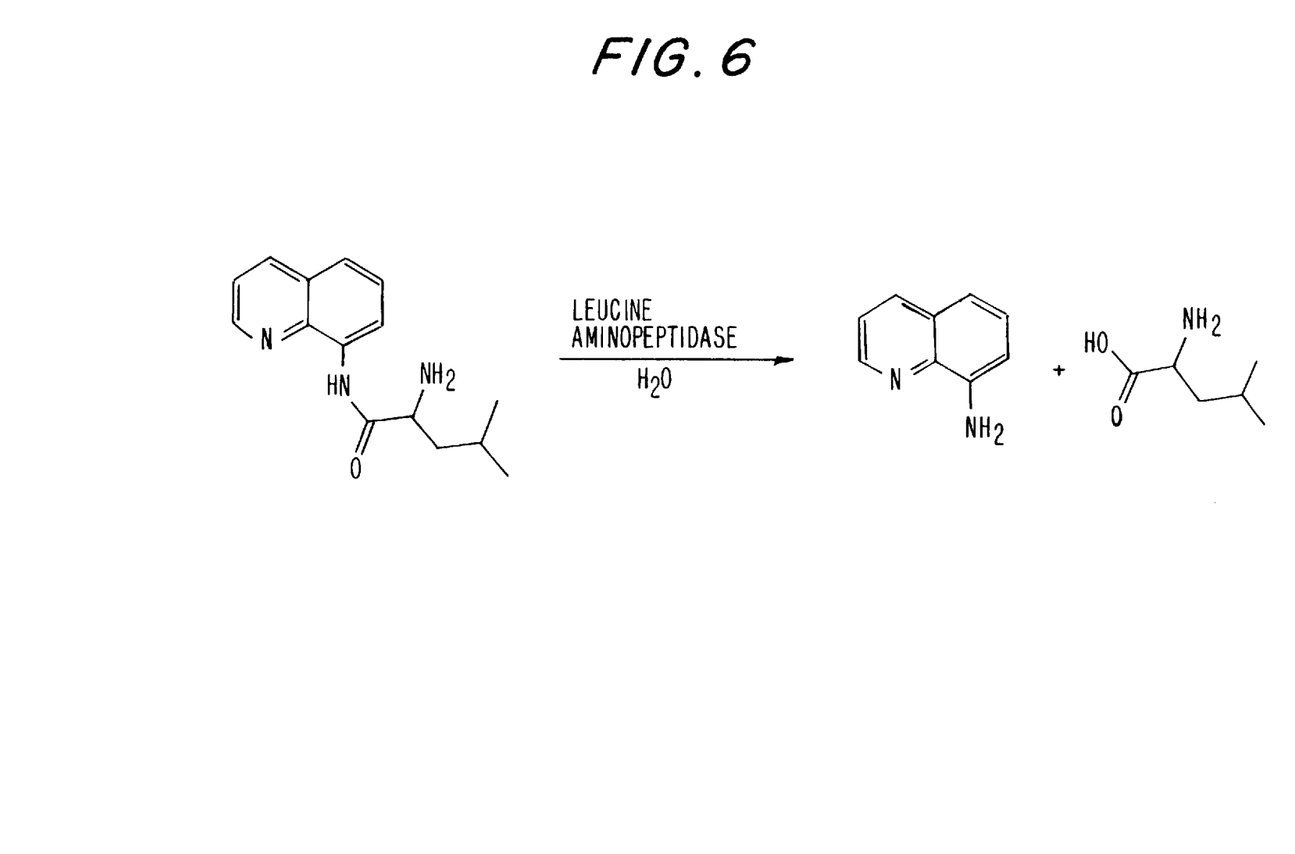
FIG. 6 shows the conversion of 8-leucyl quinoline to 8-quinoline and leucine using leucine aminopeptidase.

The proteolytic enzyme leucine aminopeptidase was detected in a second assay type. Differences in the abilities of 8-(L)-leucylaminoquinoline (9) (see Example 3) and 8-aminoquinoline (10) to form electrochemiluminescent complexes with Ru(bpy)$_2^{2+}$ (FIG. 5) (see Example 4 for experimental details) suggested that 8-(L)-leucylaminoquinoline (9) hydrolysis could form the basis of an LAP assay (Scheme 2). Surprisingly, 8-aminoquinoline (10), a well-known metal-binding agent, gave 10 time less ECL when mixed with Ru(bpy)$_2$Cl$_2$ than did its leucine derivative, 8-(L)-leucylaminoquinoline (9). Apparently, both bound Ru(bpy)$_2^{2+}$ but the complex with 8-(L)-leucylaminoquinoline (9) was more electrochemiluminescent than the complex with 8-aminoquinoline (10). This perception was strengthened by a proton NMR analysis of the isolated product of the incubation of Ru(bpy)$_2^{2+}$ with 8-(L)-leucylaminoquinoline (9), which showed that the product was substantially Ru(bpy)$_2$(9)$^{1+}$. The two complexes could be sensitively differentiated; incubation of Ru(bpy)$_2^{2+}$ with 8-(L)-leucylaminoquinoline (9) and 8-aminoquinoline (10) at 65° C. for 60 minutes resulted in complexes whose ECL differences were measurable to a lower limit of 65 nM (see Example "4.5").

Figure 2:
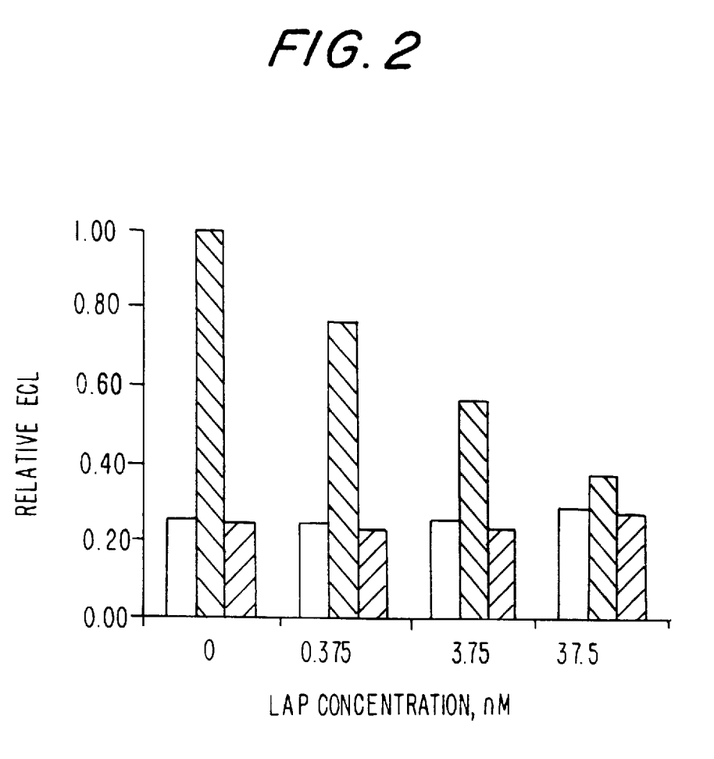
FIG. 2 illustrates ECL detection of leucine aminopeptidase (LAP). Reactions included either 13 μM of the product 8-aminoquinoline (10) plus enzyme (white bars), 13 μM of the substrate 8-(L)-leucylaminoquinoline (9) plus enzyme (grey bars), or enzyme alone (black bars). The experiment was performed according to Example 6.

LAP was found to hydrolyze 8-(L)-leucylaminoquinoline (9) to form leucine and 8-aminoquinoline (10) with a k$_{cat}$ of 369 min$^{-1}$ and a K$_m$ of 358 $\mu$M (see Example 5). LAP-catalyzed hydrolysis of 8-(L)-leucylaminoquinoline (9) was detectable by differences in the ECL of the complexes formed with Ru(bpy)$_2^{2+}$. In contradistinction to the substrate-product pair described for PLE, in this case the substrate complex with Ru(bpy)$_2^{2+}$ was substantially more electrochemiluminescent than the product complex. Because of this, enzymatic hydrolysis of 8-(L)-leucylaminoquinoline (9) was accompanied by a decrease in ECL. Using a similar experimental protocol to that described above for PLE, 375 pM LAP could be detected (FIG. 2, see also Example 6 for protocol). The difference in detection limits between LAP and PLE may be due to the necessity of including MgCl$_2$ in the LAP assay buffer. Mg$^{2+}$ presumably was bound by both 8-(L)-leucylaminoquinoline (9) and 8-aminoquinoline (10). The detection limit of substrate turnover was found to be identical for LAP as it was for PLE; 1.3 $\mu$M (data not shown).

ECL detection of enzyme-triggered changes in metal-binding ligand labelled substrates was found to be a novel and sensitive means of detecting low levels of catalysis. To test the concept, assays were carried out involving well-characterized enzymes and very simple substrates. The early success of these feasibility studies suggests that the method can be dramatically improved by more rigorous design of the ligand labelled substrates and development and optimization of detection protocols. Attractive features of ligand-labeled substrate assays are: (1) they are efficiently catalyzed by the chosen enzyme, but not other enzymes; (2) catalysis substantially alters the ability of the substrate to bind a metal and form a sensitively detectable inorganic complex; and (3) complex formation occurs rapidly under mild conditions. These assay features can be optimized either by changing the substrate structure or by changing the assay manipulations.

The ligand-labeled substrate structure can be varied to change the catalyzed (enzyme-recognized) part, the bridging linker (if any) between the catalyzed part and the ligand part, or the ligand. The enzyme-catalyzed part can be altered to look more (or less) like the natural substrate. For example, in an assay of a protease, additional amino acid residues can be added or taken away to fit the enzyme active site better. The linker can be lengthened or shortened to increase differences between metal binding abilities of the substrate and product. Moreover, the linker length may affect the enzyme's catalytic efficiency. The ligand can be changed (see for example, picolinic acid (1) versus 8-aminoquinoline (10)). Changing the ligand could affect the binding and subsequent ECL properties of the complex of the substrate or product with metals. Because of the empirical nature of each of these three factors (catalyzed portion, linker portion, and ligand portion) in this novel ECL assay, each may be systematically altered to achieve the optimal combination for a desired enzyme assay. For each enzyme assay, the choice of the three components might depend on the particular assayed enzyme.

Assay manipulations that can be altered include: (1) changes in the enzyme reaction conditions; (2) changes in the ligand-binding conditions; or (3) changes in the detection conditions. The enzyme assay conditions might be altered to increase the rate of the reaction (by altering pH, and other common assay parameters) and also to decrease the presence of any materials (such as extraneous metal binding ligands) that might harm ligand binding or detection. The ligand binding conditions might be improved by changing the time, temperature, by adding organic cosolvents, by using photochemical means, or by changing the metal's leaving group. The detection conditions might be altered by using a method other than ECL, or if ECL is used, by changing ECL parameters such as the maximum voltage applied, the voltage ramping or stepping speed, or the PMT voltage. The structures of substrates and products can be optimized for a rapid rate of turnover by a chosen enzyme, for dramatic differentiation between the substrates' and products' abilities to form electrochemiluminescent complexes with Ru(bpy)$_2^{2+}$, and for optimal thermodynamic and kinetic parameters in metal complex formation. If the inorganic complex and analytical method is carefully chosen, for example by using electrochemiluminescent ruthenium complexes as described here, picomolar or lower concentrations of product should be detectable with low background signal. The examples described in this application of pig liver esterase and leucine aminopeptidase were shown to give highly sensitive detection with little optimization, using extremely simple compounds made by elementary synthetic procedures. With greater synthetic effort (for example, making a dipeptide derivative for leucine aminopeptidase instead of a single derivative) the substrates may be better recognized by the enzyme, bind better and faster to the metal, and may be more sensitively detected.

Electrochemical Detectants

Organic compounds which are suitable electrochemical detectants include, for example, rubrene and 9,10-diphenyl anthracene. Many organometallic compounds are suitable electrochemical detectants. However, Ru-containing compounds, such as ruthenium II tris-bipyridine chelate, and Os-containing compounds are preferred. Detectants useful in the presently disclosed invention can be found in U.S. Pat. No. 5,310,687.

These detectants are stable for long periods. In addition, the detectants are safe and relatively inexpensive. They give a highly characteristic signal and do not occur in nature. Measurements based on luminescence of such detectants are sensitive, fast, reproducible and utilize simple instrumentation. The signal is generated repeatedly by each molecule of the detectant, thereby enhancing the sensitivity with which these detectants may be detected. The preferred electrochemiluminescent detectants of the present invention are conveniently referred to herein as $Ru(bpy)_3^{2+}$. Various amounts of this detectant, or its equivalent, may be employed. These detectants can be used directly in a variety of samples, e.g. biological, food, without pretreatment of the sample.

Suitable enzymes

Although the method is described as being most useful for detecting hydrolytic enzymes, non-hydrolytic enzymes may also be detected by this method (as a general reference see: Enzymes, M. Dixon & E. C. Webb, 3rd ed. 1979, Academic Press, New York).

For example, oxidoreductases could be detected. These enzymes oxidize or reduce substrates using a co-substrate or cofactor such as NADH, $O_2$, or $FADH_2$ as an electron acceptor/donor. One common dehydrogenase reaction is the oxidation of an aldehyde (a weaker metal-binding group) to a carboxylic acid (a stronger metal-binding group) (see Compounds 1 vs. 2 in FIG. 3). Detection of such dehydrogenases would involve using substrates that when oxidized would bind to $Ru(bpy)_2^{2+}$ and the resulting complex would be electrochemiluminescent. For example, aldehyde dehydrogenases (EC 1.2.1) could convert 2-pyridinecarboxaldehyde (2) to picolinic acid (1) with concomitant reduction of $NAD(P)^+$.

Transferases could also be detected by their ability to chemically modify a substrate which could bind to $Ru(bpy)_2^{2+}$ to form an electrochemiluminescent mixed-ligand complex. One example is fatty-acid methyltransferase (EC 2.1.1.15) which transfers a methyl group from S-adenosyl-L-methionine to fatty acids to form fatty acid methyl esters. The anionic carboxylic acid substrates will be better metal-binding agents than the neutral methyl ester products. Compounds such as picolinic acid (1) could be substrates for this enzyme.

Lyases (enzymes that non-hydrolytically cleave C-C, C-O, C-N, and other bonds) could also be detected by this method. For example, many lyases are carboxy-lyases (EC 4.1.1) which remove the carboxylic acid group from compounds (R-COOH) to form $CO_2$ and R-H. Because carboxylates can bind to metals such as ruthenium, $R-COO^-$ could bind to $Ru(bpy)_2^{2+}$ to form an electrochemiluminescent complex but R-H (or $CO_2$) could not. Compounds similar to picolinic acid (1) could be used. Structural modifications, based on prior knowledge of substrate specificity, may be made to improve recognition by a chosen enzyme.

Isomerases, which catalyze changes within a single molecule, could also be detected by this method. For example, (EC 5.1.1) are enzymes that catalyze amino acid chiral inversions (L-to-D, or D-to-L). The chirality of an amino acid or a derivative thereof can affect the way it binds to a metal complex, especially asymmetric complexes. In this assay an enzyme would alter the chirality of an amino acid or a derivative of an amino acid (as in the leucine derivatives shown in FIG. 5 ((L)-leucylaminoquinoline (9) and CB2-8-(L)-leucylaminoquinoline (11)). In (L)-leucylaminoquinoline (9), leucine is present as the L isomer. If an enzyme altered this substrate to a D version, the compound would bind differently and with altered affinity to some ruthenium complexes, especially asymmetric complexes. The resulting mixed ligand complexes (L vs. D) will differ in ECL properties.

Metal binding ligands

Suitable metal binding ligands include aromatic and aliphatic polydendate ligands such as bipyridyl, bipyrazyl, terpyridyl, phenanthrolyl and porphyrins. These polydentate ligands may be unsubstituted or substituted by any of a large number of substituents including for example, alkyl, substituted alkyl, aryl, substituted aryl, aralkyl, substituted aralkyl, carboxylate, carboxyaldehyde, carboamide, cyano, amino, hydroxy, imino, hydroxycarbonyl, amino hydroxy, imono hydroxycarbonyl, amino carbonyl, amidine, guanidinium, ureide, maleimide sulfur-containing groups, phosphorous containing groups and the carboxylate ester of N-hydroxysuccinimide.

Mixed Ligand Complex Detectant Formation

During complex formation, one relatively loosely-bound ligand on the metal complex (such as $Cl^-$ in $Ru(bpy)_2^{2+}$ $Cl^-$ or $H_2O$ in $Ru(bpy)_2^{2+}$ $H_2O$ is displaced by a second, more tightly binding ligand (such as picolinic acid (1) or 8-aminoquinoline (10)). Complex formation requires dissociation of the first ligand, which may be rate-limiting and association of the second ligand, which also may be rate-limiting. The rates of displacement are usually temperature dependent, occurring at a faster rate at higher temperatures.

The complexes can be slowly formed at room temperature in aqueous solvent. Elevated temperatures greatly increase the rate of formation. Room temperature formation may require 24 hours or longer while temperatures of 45°, 65°, or 85° C. may reduce the time required to one hour or less. Other means of complex formation may be to include an organic co-solvent (1:1 methanol-water, ethanol-water, acetone-water) or to use photochemical rather than thermal synthesis. Complex formation may be also facilitated by using, instead of the chloride salt of $Ru(bpy)_2^{2+}$, a better leaving group such as cyclootadiene or triflate anion. The best way of forming the appropriate complex can be determined by one skilled in the art by experimenting with temperature, photochemical synthesis, leaving ligand, and organic co-solvents using established protocols. (See as a general review, R. A. Krause, Structure & Bonding, supra.)

Generation of or Inhibition of Chemiluminescence $Ru(bpy)_3^{2+}$ and tripropylamine are oxidized at the surface of a gold electrode, forming $Ru(bpy)_3^{3+}$ and tripropylamine-derived cation radical, respectively. The tripropylamine-derived cation radical spontaneously loses a proton, forming tripropylamine-derived neutral radical. The tripropylamine-derived neutral radical, a strong reductant, reacts with $Ru(bpy)_3^{3+}$, a strong oxidant, forming the excited state of the detectant, $Ru(bpy)_3^{2+*}$. The excited state decays to the ground state through a normal fluorescence mechanism, emitting a photon having a wavelength of 620 nm.

Electrochemilumenescent Measurement and Apparatus

The energy necessary for formation of the excited state arises from the large difference in electrochemical potentials of the $Ru(bpy)_3^{3+}$ and the tripropylamine-derived neutral radical. The excited-state $Ru(bpy)_3^{2+*}$ decays through a normal fluorescence mechanism, emitting a photon at 620 nm. This process regenerates the original form of the $Ru(bpy)_3^{2+}$, which is free to cycle multiple times through the reaction sequence. Each ECL-active detectant, therefore, can emit many photons during each measurement cycle, thereby enhancing detection.

Quantification of the $Ru(bpy)_3^{2+}$ detectant can be readily automated with relatively uncomplicated instrumentation. The heart of an instrument is the electrochemical flow-cell, containing the working electrodes and counter electrodes for initiation of the ECL reaction. Both of the electrodes are fabricated from gold, but other materials have been used with various degrees of success. A potentiostat applies various voltage waveforms to the electrodes, and a single photomultiplier tube (PMT) detects the light emitted during the ECL reaction. An Ag/AgCl reference electrode is placed in the fluid path downstream from the flow cell, and a peristaltic pump is used to draw various fluids through the flow cell. In a typical sequence, the assay fluid is drawn from a test tube into the flow cell and the detectant is quantified by applying a ramp voltage to the electrodes and measuring the emitted light. After the measurement, a high-pH cleaning solution is drawn into the cell for an electrochemical cleaning procedure. A conditioning solution is then drawn into the cell, and a voltage waveform is applied that leaves the surfaces of the electrodes in a highly reproducible state, ready for the next measurement cycle.

The ECL reaction can be efficiently initiated by many different voltage waveforms. Measurements of the working electrode current and the ECL intensity are induced by the application of a triangle wave to the electrodes. The applied voltage as shown is actually the voltage measured at the Ag/AgCl reference electrode and includes the effects of a significant uncompensated resistance; consequently, the actual voltage applied at the working electrode is substantially less than that depicted. The triangle waveform rises from 565 to 2800 mV at a rate of 750 mV/s and then decreases at the same rate to 1000 mV. The current that flows in the cell is primarily the result of the oxidation of the tripropylamine and the ruthenium metal complex and the hydrolysis of water. Oxidation of both the tripropylamine and $Ru(bpy)_3^{2+}$ becomes evident when the applied voltage reaches ~1100 mV and produces a luminescence. The intensity of the luminescence increases with the applied voltage until the tripropylamine at the surface of the electrode is depleted, resulting in decreased intensity. The intensity of the observed luminescence is great enough that it can easily be measured with conventional PMTs operating either in photon-counting or current modes.

The sample and reagents are placed in a measuring cell to obtain a baseline reading. Typically the reagents are added in concentrations between 10 micromolar and 1.0 millimolar. The electrochemiluminescent detectant is typically present at $10^{-6}M$ concentrations (range 1–15 $\mu M$). The sample containing cell is then incubated for a sufficient period of time to insure that catalyzed hydrolysis can occur if the enzyme is present. This period of time typically varies between 5 minutes and 4 hours. Longer and shorter periods of time are possible depending on sample and reagent concentrations. Since all that is involved is empirical parameters, their values can be determined using conventional techniques.

After incubation occurs, a second reading is taken. The difference in readings, if any, correlates with the hydrolase activity present in the sample.

After the sample is contacted with reagent and/or incubated, the ECL measurement is performed by application of electrical potential to the working electrode. This gives a characteristic signal from the emitted light. Relatively little interference results from background presented by the other materials present in the sample or added buffer.

Accordingly, the apparatus and methodology suitable for the performance of the process of this invention include, as noted earlier, those shown in U.S. Pat. Nos. 5,068,088, 5,061,455, 5,093,268, and 5,147,806 and 5,221,605. In addition, electrochemiluminesence molecules for use in the measuring system as detectants include those bidentate aromatic heterocyclic nitrogen-containing ligands of ruthenium and osmium described in U.S. Pat. Nos. 5,310,687 and 5,310,687.

Reagent (Test) Kits

Reagent kits containing the materials necessary for the performance of the assays can be assembled to facilitate handling, and foster standardization. Materials to be included in the kit may vary depending on the ultimate purpose. Typically the kit would include the electrochemiluminescent detectant or other detectant appropriate for the measuring technique selected, ligand labelled enzyme substrate or ligand substrate, and necessary buffers. Other reagents such as standards could also be included. The standards can be chemical reagents or empirical data in printed or electronic form necessary for the calibration, if necessary, or the performance of the assay.

EXAMPLES

Example 0.5

A mixture of 400 $\mu M$ $Ru(bpy)_2Cl_2$ and 130 $\mu M$ ligand in 80 mM sodium phosphate, pH 7.6, was heated in a 65° C. water bath for 60 minutes. Following 2000-fold dilution into standard instrument buffer (IGEN, Inc., Gaithersburg, Md.), ECL was measured using an IGEN Origen® Analyzer (IGEN, Inc., Gaithersburg, Md.).

Example 1

PLE-catalyzed hydrolysis of 2-pyridinecarboxylic acid ethyl ester (4) was characterized spectrophotometrically at 290 nm ($\Delta E_{290}$=25,500 $M^{-1}cm^{-1}$). Enzyme reactions were performed at 25.0°±0.1° C. in 0.5 M sodium phosphate, pH 8.0, containing 10% DMF and were monitored using a Hitachi U-3200 spectrophotometer (Danbury, Conn.). During kinetics studies, PLE concentration was 270 nM and 2-pyridinecarboxylic acid ethyl ester (4) concentration varied from 10 to 350 $\mu M$. Kinetic constants were obtained by computer fitting directly to the Michaelis-Menten equation using Kaleidagraph (Abelbeck Software, Reading, Pa.).

Example 1.5

Detection of the ECL differences between 65 pM picolinic acid (1) and 2-pyridinecarboxylic acid ethyl ester (4). A mixture of 400 $\mu M$ $Ru(bpy)_2Cl_2$, 0.13 $\mu M$ picolinic acid (1) or 2-pyridinecarboxylic acid ethyl ester (4), and 80 mM sodium phosphate, pH 7.6, was heated in a 65.0° C. water bath for 60 minutes. Following 2000-fold dilution into instrument buffer, ECL was measured.

Example 2

For ECL analysis of low levels of PLE activity, 2-pyridinecarboxylic acid ethyl ester (4) (generally 13 $\mu M$) and various concentrations of the enzyme was incubated overnight at 37.0°±0.1° C. in 50 nM phosphate, pH 8.0. Following the enzyme reaction, $Ru(bpy)_2^{2+}$ was added to a final concentration of 400 $\mu M$ and the solution was heated at 65° C. for 3.5 hours to facilitate complex formation. Finally, the ECL of the mixture was measured using an Origen® Analyzer (IGEN, Inc., Gaithersburg, Md.).

Example 3

A solution of 8-aminoquinoline (1 g, 6.9 mmol) and N-CBZ-L-leucine (2.2 g, 8.3 mmol) in dry methylene chloride (35 mL) was mixed with 1-hydroxybenzotriazole (1.1 g, 8.3 mmol) and 1-ethyl-3-(3-dimethylaminopropyl) carbodiimide hydrochloride (1.6 g, 8.3 mmol) . The reaction mixture was stirred overnight at room temperature and then worked up with saturated sodium chloride, saturated sodium bicarbonate, and water. The organic layer was dried with magnesium sulfate. Following solvent removal, product was purified by column chromatography on silica gel eluted with hexane-ethyl acetate (4:1) to give pure CBZ-L-leucine aminoquinoline. It was deprotected by treating it with hydrogen gas and 10% palladium on carbon in ethyl acetate to give pure 8-(L)-leucylaminoquinoline (60% yield).

Example 4

A mixture of 400 μM Ru(bpy)$_2$Cl$_2$ and 130 μM ligand in 80 mM sodium phosphate, pH 7.6, was heated in a 65° C. water bath for 60 minutes. Following 20-fold dilution into standard instrument buffer (IGEN, Inc., Gaithersburg, Md.), ECL was measured using an IGEN Origen® Analyzer (IGEN, Inc., Gaithersburg, Md.).

Example 4.5

Detection of the ECL differences between 65 nM 8-(L)-leucylaminoquinoline (9) and 8-aminoquinoline (10) . A mixture of 400 μM Ru(bpy)$_2$Cl$_2$, 0.13 mM 8-(L)-leucylaminoquinoline (9) or 8-aminoquinoline (10), and 80 mM sodium phosphate, pH 7.6, was heated in a 65.0° C. water bath for 60 minutes. Following 2000-fold dilution into instrument buffer, ECL was measured.

Example 5

Kinetic characterization LAP-catalyzed hydrolysis of 8-(L)-leucylaminoquinoline (9) was carried out at 37°±0.1° C. in 90 mM sodium phosphate, pH 7.6, containing 10% DMF. Activity was spectrophotometrically monitored at 300 nm ($\Delta E_{300}$=40,200 M$^{-1}$cm$^{-1}$. LAP concentration was 76 μM and 8-(L)-leucylaminoquinoline (9) was varied from 5 to 400 μM. Kinetic constants were obtained by computer fitting directly to the Michaelis-Menten equation using Kaleidagraph (Abelbeck Software, Reading, Pa.).

Example 6

For ECL analysis of low levels of LAP activity, 8-(L)-leucylaminoquinoline (9) (generally 13 μM) and various concentrations of the enzyme was incubated overnight at 37.0°±0.1° C. in 100 mM phosphate, pH 8.0, containing 5.0 mM MgCl$_2$. Following the enzyme reaction, Ru(bpy)$_2$$^{2+}$ was added to a final concentration of 400 μM and the solution was heated at 65° C. for 3.5 hours to facilitate complex formation. Finally, the ECL of the mixture was measured using an Origen® Analyzer (IGEN, Inc., Gaithersburg, Md.).

Example 7

Besides ECL, other methods can be used to detect alterations in the structures of mixed ligand inorganic complexes that contain ligands that are substrates or products of enzymes. These methods include but are not limited to: UV, visible, or IR absorption, NMR, CD, MCD, EPR, and MS.

Figure 7:
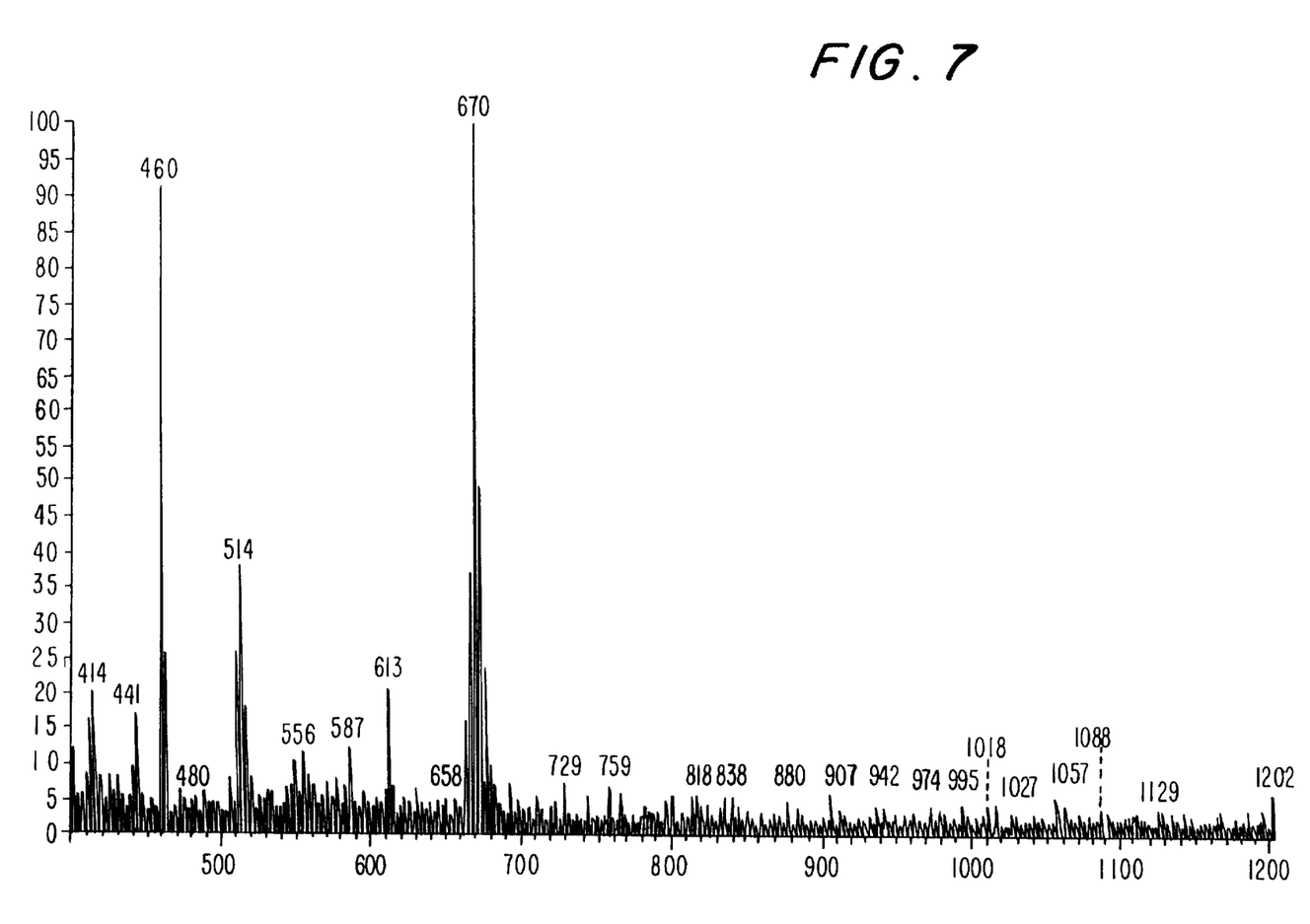
FIG. 7 shows the mass spectrum of Ru(bpy)$_2$$^{2+}$. The peak of mass 670 corresponds to Ru(bpy)$_2$$^{2+}$(minus 2×PF$_6$).

To demonstrate the use of mass spectroscopy (MS), the formation of the complex of Ru(bpy)$_2$$^{2+}$ with the substrate of leucine aminopeptidase, 8-leucylaminoquinoline (10) is observed. 8-Leucylaminoquinoline (52 mg) and Ru(bpy)$_2$Cl$_2$ (90 mg) were mixed in 3.5 mL of a 1:1 mixture of ethanol and sodium phosphate buffer (0.1M, pH 7.6). The mixture was then refluxed for 5 hours. Ethanol was removed by evaporation and the formed mixed ligand complex, Ru(bpy)$_2$$^{2+}$, was isolated using sp-Sephadex and a stepwise NaCl gradient (0.1 mM, 1 mM, 10 mM, 50 mM, 60 mM, 100 mM, 110 mM, 120 mM, and 130 mM). An eluted peak, believed to be Ru(bpy)$_2$$^{2+}$, was shown by NMR to contain the correct functional groups. The compound was extracted by CH$_2$Cl$_2$/H$_2$O with added ammonium hexafluorophosphate (PF$_6$). The resulting salt was analyzed by mass spec. The mass spectrum (FIG. 7) showed that the compound was indeed Ru(bpy)$_2$$^{2+}$ (M-Scan, Inc. (West Chester, Pa.)). The peak of mass 670 corresponds to Ru(bpy)$_2$$^{2+}$ (minus 2×PF$_6$. This example shows that mixed ligand complexes containing, as one of the ligands, an enzyme substrate, can be detected by means other than ECL.

Example 8

Mixed ligand complexes can be formed from transition metals such as cobalt (II). An example of a ligand that can bind to transition metals is 8-aminoquinoline. Cobalt (II) complexes are visibly colored (generally pink) and the wavelengths and magnitudes of the peaks in the corresponding visible absorption spectra vary substantially based on the identity of the bound ligands (S. A. Latt and B. L. Vallee, Biochemistry (1971) 10, 4263–4270; B. Holmquist, T. A. Kaden, B. L. Vallee, Biochemistry (1975), 14, 1454–1461). Because of this, leucine aminopeptidase can be detected by its ability to hydrolyze 8-leucylaminoquinoline 8-aminoquinoline (10) to form leucine and 8-(L)-leucylaminoquinoline (9). Mixed ligand cobalt (II) complexes that include the substrate, 8-aminoquinoline (10) , an the product, 8-(L)-leucylaminoquinoline (9), will have different visible absorbance spectra and can be distinguished. Cobalt complexes that can be used in such detection assays include Co(Cl$_4$)$^{-2}$, Co(OH)$_4$$^{2-}$, CoSO$_4$, Co(NO$_3$)$_2$, Co(Imidazole)$_3$(H$_2$O)$^{+2}$, Co(Et$_4$dien)Cl$_2$, and Co(mc$_6$Tren)Br$_2$. Other colored metals whose visible absorbance spectra is affected by metal binding ligands may also be used including iron (II) and copper (II).

Cobalt (II) is described here as an example of a metal whose visible absorbance spectra in complexes can be used to detect enzyme activity. As described above, compound 8-aminoquinoline (10) is a good substrate of leucine aminopeptidase (LAP). The action of LAP releases leucine from 8-aminoquinoline (9). As described above, a solution that may contain LAP is mixed with a solution of 8-aminoquinoline (10). After a time sufficient for hydrolysis of 8-aminoquinoline (10) to occur (depending on the nature of the sample and suspected presence of LAP, the time could be from 1 minute to 24 hours), the reaction mixture is further mixed with a solution of a cobalt complex that is able to bind 8-(L)-leucylaminoquinoline (9) and 8-aminoquinoline (10). A good choice would be Co(Cl$_4$)$^{2-}$. The concentration of Co(Cl$_4$)$^{2-}$ could be from 1–500 μM, but may be best around 10 μM. Upon heating of this mixture at 65° C. for 60 minutes, both 9 and 8-aminoquinoline (10) may bind to cobalt by displacing a chloride ion in Co(Cl)$_4$$^{2-}$, However, because of their different affinities with different electronic effects on the d orbital electrons of cobalt atom, they will form complexes with different visible spectra when recorded in a visible spectrophotometer. Thus, after complex formation a visible spectrophotometric scan from 700 nm to 400 nm will demonstrate whether 8-(L)-leucylaminoquinoline (9) or 8-aminoquinoline (10) has bound to cobalt and hence whether LAP is present and catalytically active. The extent of the spectral change can be used to quantitate LAP in the unknown solution. For quantitate, several parameters may require optimization, the primary parameter will be the length of time the enzyme solution is allowed to react with substrate before complex formation. Such parameter optimization is accomplishable by one skilled in the art.

Although the examples illustrate various modifications of the present invention, other variations will suggest themselves to those skilled in the art in light of the above disclosure. It is to be understood, therefore, that changes may be made in the particular embodiments described above which are within the full intended scope of the inventions as defined in the appended claims.

What is claimed is:

1. A kit for measuring an enzyme analyte comprising a
   (a) a metal binding ligand derivative selected from the group consisting of (i) a metal binding ligand labelled substrate and (ii) a metal binding ligand substrate and
   (2) an electrochemical detectant selected from the group consisting of (i) Ru-containing compounds and (ii) Os-containing compounds
   such that the metal binding ligand derivative and the enzyme are capable, when contacted with one another, of reacting to form a metal binding ligand that interacts with the electrochemical detectant to form a mixed ligand complex having an altered electrochemiluminescent signal.

2. The kit according to claim 1 wherein the metal binding ligand derivative is a metal binding ligand labelled substrate.

3. The kit according to claim 2 wherein the metal binding ligand labelled substrate is a metal binding ligand labelled hydrolase substrate wherein the metal binding ligand labelled hydrolase substrate is acted upon by the hydrolase to release the metal binding ligand.

4. The kit according to claim 3 wherein the metal binding ligand labelled hydrolase substrate is 8-(L)-leucylaminoquinoline.

5. The kit according to claim 3 wherein the metal binding ligand labelled hydrolase substrate is picolinic acid alkyl ester.

6. The kit according to claim 1 wherein the enzyme is a hydrolase.

7. The kit according to claim 6 wherein the hydrolase is an esterase or aminopeptidase.

8. The kit according to claim 7 wherein the aminopeptidase is leucine aminopeptidase.

9. The kit according to claim 7 wherein the esterase is pig liver esterase.

10. The kit according to claim 1 wherein the Ru-containing compounds and Os-containing compounds are metal binding ligand complexes wherein the ligands are selected from the group of aromatic and aliphatic polydendate ligands.

11. The kit according to claim 10 wherein the aromatic and aliphatic polydendate ligands are selected from the group consisting of bipyridyl, bipyrazyl, terpyridyl, phenanthrolyl, porphyrins and substituted derivatives thereof.

12. The kit according to claim 11 wherein the derivative substituents are selected from alkyl, substituted alkyl, aryl, substituted aryl, aralkyl, substituted aralkyl, carboxylate, carboxyaldehyde, carboamide, cyano, amino, hydroxy, imino, hydroxycarbonyl, amino hydroxy, imono hydroxycarbonyl, amino carbonyl, amidine, guanidinium, ureide, maleimide sulfur-containing groups, phosphorous containing groups and the carboxylate ester of N-hydroxysuccinimide.

13. The kit according to claim 1 wherein the metal binding ligand derivative is a metal binding ligand labelled substrate.

14. The kit according to claim 13 wherein the metal binding ligand labelled substrate is selected from the group consisting of 2-pyridinecarboxylic acid (picolinic acid), 2-pyridinecarboxalehyde, 2-mercaptopyridine, 2-pyridinecarboxylic acid ethyl ester, 2-pyridylcarbinol, 2-pyridinecarboxamide (picolinamide), 3-pyridylcarbinol, and 4-pyridylcarbinol.

15. A method for measuring an enzyme analyte comprising,
   (a) contacting a sample suspected of containing the enzyme with a metal binding ligand derivative selected from the group consisting of a metal binding ligand labelled substrate or a metal binding ligand substrate and electrochemical detectants selected from the group consisting of Ru-containing compounds and Os-containing compounds;
   (b) incubating the contacted sample under conditions that cause the enzyme, if present, to act on the metal binding ligand derivative to form a ligand that combines with the electrochemical detectant to form a mixed ligand complex having an altered electrochemiluminescent signal;
   (c) subjecting the incubated sample of step (b) to conditions which result in electrochemiluminesence; and
   (d) measuring the resulting electrochemiluminescence
   (e) comparing the measurements of steps (d) with a baseline reading to ascertain the amount of enzyme present in the sample.

16. The method of claim 15 wherein the steps are performed in a single container.

17. The method of claim 15 wherein the enzyme is a hydrolase.

18. The method of claim 17 wherein the hydrolase is selected from aminopeptidase or esterase.

19. The method according to claim 18 wherein the aminopeptidase is leucine aminopeptidase.

20. The method according to claim 18 wherein the esterase is pig liver esterase.

21. The method according to claim 15 wherein the metal binding ligand derivative is a metal binding ligand labelled substrate.

22. The method according to claim 21 wherein the metal binding ligand labelled substrate is a metal binding ligand labelled hydrolase substrate wherein the metal binding ligand derivative is acted upon by the hydrolase to form the metal binding ligand.

23. The method according to claim 22 wherein the metal binding ligand labelled hydrolase substrate is 8-(L)-leucylaminoquinoline.

24. The method according to claim 22 wherein the metal binding ligand labelled hydrolase substrate is picolinic acid alkyl ester.

25. The method according to claim 22 wherein the metal binding ligand labelled hydrolase substrate is selected from the group consisting of 2-pyridinecarboxylic acid (picolinic acid), 2-pyridinecarboxalehyde, 2-mercaptopyridine, 2-pyridinecarboxylic acid ethyl ester, 2-pyridylcarbinol, 2-pyridinecarboxamide (picolinamide), 3-pyridylcarbinol, and 4-pyridylcarbinol.

26. The method according to claim 22 wherein the metal binding ligand labelled hydrolase substrate is selected from the group consisting of 8-(L)-leucylaminoquinoline, 8-aminoquinoline and CB2-8-(L)-leucylaminoquinoline.

27. The method of claim 15 wherein the Ru-or Os-containing compound is a bidentate aromatic heterocyclic nitrogen- containing ligand of ruthenium or osmium.

28. The method of claim 27 wherein the bidentate aromatic heterocyclic nitrogen- containing ligand of ruthenium or osmium is selected from the group consisting $Ru(bpy)_3^{2+}$ reagent and $Os(bpy)_3^{2+}$.

29. The method according to claim 15 wherein the Ru-containing compounds and Os-containing compounds are ligand complexes wherein the ligand is selected from the group of aromatic and aliphatic polydendate ligands.

30. The method according to claim 29 wherein the aromatic and aliphatic polydendate ligands are selected from the group consisting of bipyridyl, bipyrazyl, terpyridyl, phenanthrolyl, porphyrins and substituted derivatives thereof.

31. The method according to claim 30 wherein the derivative substituents are selected from alkyl, substituted alkyl, aryl, substituted aryl, aralkyl, substituted aralkyl, carboxylate, carboxyaldehyde, carboamide, cyano, amino, hydroxy, imino, hydroxycarbonyl, amino hydroxy, imono hydroxycarbonyl, amino carbonyl, amidine, guanidinium, ureide, maleimide sulfur-containing groups, phosphorous containing groups and the carboxylate ester of N-hydroxysuccinimide.

32. The method according to claim 15 wherein the Ru-containing compound is ruthenium (II) bis(bipyridyl).

33. A method for measuring an enzyme analyte comprising,
  (a) contacting a sample suspected of containing the enzyme with a metal binding ligand derivative selected from the group consisting of a metal binding ligand labelled substrate or a metal binding ligand substrate and a detectant mixed ligand complex selected from the group consisting of cobalt (II)-containing complexes, iron (II) complexes, copper (II) complexes, Co-containing compounds, Fe-containing compounds, Ru-containing compounds and Os-containing compounds;
  (b) incubating the contacted sample under conditions that cause the enzyme, if present, to act on the metal binding ligand derivative to form a ligand that combines with the electrochemical detectant to form a mixed ligand complex;
  (c) measuring the mixed ligand complex formed in step (c) using a measuring technique selected from the group consisting of UV, visible, or IR absorption, NMR, CD, MCD, EPR, ECL and MS, and
  (d) determining the amount of enzyme present in the sample based on the measurement of step (c).

34. The method for measuring an enzyme analyte of claim 33 wherein the cobalt complex is selected from the group consisting of $Co(Cl_4)^{-2}$, $Co(OH)_4^{2-}$, $CoSO_4$, $Co(NO_3)_2$, $Co(Imidazole)_3(H_2O)^{+2}$, $Co(Et_4dien)Cl_2$, and $Co(mc_6Tren)Br_2$.

35. The method for measuring an enzyme analyte of claim 34 wherein the cobalt complex is $Co(Cl_4)^{2-}$.

36. The method of claim 33 wherein the steps are performed in a single container.

37. The method of claim 33 wherein the enzyme is a hydrolase.

38. The method of claim 37 wherein the hydrolase is selected from aminopeptidase or esterase.

39. The method according to claim 38 wherein the aminopeptidase is leucine aminopeptidase.

40. The method according to claim 38 wherein the esterase is pig liver esterase.

41. The method according to claim 33 wherein the metal binding ligand derivative is a metal binding ligand labelled substrate.

42. The method according to claim 41 wherein the metal binding ligand labelled substrate is a metal binding ligand labelled hydrolase substrate wherein the metal binding ligand derivative is acted upon by the hydrolase to form the metal binding ligand.

43. The method according to claim 42 wherein the metal binding ligand labelled hydrolase substrate is 8-(L)-leucylaminoquinoline.

44. The method according to claim 42 wherein the metal binding ligand labelled hydrolase substrate is picolinic acid alkyl ester.

45. The method according to claim 42 wherein the metal binding ligand labelled hydrolase substrate is selected from the group consisting of 2-pyridinecarboxylic acid (picolinic acid), 2-pyridinecarboxalehyde, 2-mercaptopyridine, 2-pyridinecarboxylic acid ethyl ester, 2-pyridylcarbinol, 2-pyridinecarboxamide (picolinamide), 3-pyridylcarbinol, and 4-pyridylcarbinol.

46. The method according to claim 42 wherein the metal binding ligand labelled hydrolase substrate is selected from the group consisting of 8-(L)-leucylaminoquinoline, 8-aminoquinoline and CB2-8-(L)-leucylaminoquinoline.

47. The kit according to claim 13, wherein the metal binding ligand labelled substrate is selected from the group consisting of 8-(L)-leucylaminoquinoline, 8-aminoquinoline and CB2-8-(L)-leucylaminoquinoline.

48. The kit according to claim 1 wherein the Ru-containing compound is ruthenium (II) bis(bipyridyl).

* * * * *